United States Patent [19]

Wang et al.

[11] Patent Number: 5,427,960
[45] Date of Patent: Jun. 27, 1995

[54] FLUORESCENCE POLARIZATION ASSAY FOR CYCLOSPORIN A AND METABOLITES AND RELATED IMMUNOGENS AND ANTIBODIES

[75] Inventors: Nai-Yi Wang, Mundelein; Philip P. Wang, Libertyville; Marjorie A. Morrison, Grayslake, all of Ill.

[73] Assignee: Abbott Laboratories, Abbott Park, Ill.

[21] Appl. No.: 318,570

[22] Filed: Oct. 5, 1994

Related U.S. Application Data

[60] Continuation of Ser. No. 60,598, May 12, 1993, abandoned, which is a division of Ser. No. 776,890, Oct. 15, 1991, Pat. No. 5,239,057, which is a continuation of Ser. No. 376,244, Jul. 6, 1989, abandoned, which is a continuation of Ser. No. 31,494, Mar. 27, 1987, abandoned.

[51] Int. Cl.⁶ .................... G01N 33/52; G01N 33/53; G01N 33/58; G01N 33/68
[52] U.S. Cl. .................... 436/536; 436/501; 436/546; 436/805; 436/815; 530/321
[58] Field of Search .............. 436/536, 546, 501, 805, 436/815; 530/321

[56] References Cited

U.S. PATENT DOCUMENTS

| | | | |
|---|---|---|---|
| 4,117,118 | 9/1978 | Harri et al. | 514/11 |
| 4,288,431 | 9/1981 | Traber et al. | 530/321 |
| 4,289,851 | 9/1981 | Traber et al. | 530/321 |
| 4,396,542 | 8/1983 | Wenger | 530/321 |
| 4,420,568 | 12/1983 | Wang et al. | 436/536 |
| 4,476,229 | 10/1984 | Fino et al. | 436/500 |
| 4,510,251 | 4/1985 | Kirkemo et al. | 436/536 |
| 4,727,035 | 2/1988 | Mahoney | 436/518 |

FOREIGN PATENT DOCUMENTS

86/02080 4/1986 WIPO.

OTHER PUBLICATIONS

Wenger, R. M. *Cyclosporine and Analogues—Isolation and Synthesis—Mechanism of Action and Structural Requirements for Pharmacological Activity*, Progress in the Chemistry of Organic Natural Products, vol. 50 (1986) pp. 123–168.

Rudinger, *Characteristics of the Amino Acids s Components of a Peptide Hormone Sequence*, Peptide Hormones, Parsons (Ed.), U. Park Press, Baltimore, pp. 1–7 (1976).

Sandoz, Ltd., *Ciclosporin RIA-KIT*, pp. 1–23 (Feb. 1983).

Carruthers et al., *Simplified Liquid-Chromatographic Analysis for Cyclosporin A, and Comparison with Radioimmunoassay*, Clin. Chem., vol. 29, No. 1, pp. 180–183 (1983).

Donatsch et al., *A Radioimmunoassay to Measure Cyclosporin A in Plasma and Serum Samples*, Chem Abstr., vol. 95, No. 197042f (1981).

Rich et al., *Synthesis and Antimitogenic Activities of four Analogs of Cyclosporin A Modified in the 1-Position*, Chem. Abstr., vol. 104, No. 207665g (1986).

Donatsch et al., Journal of Immunoassay, vol 2(1), pp. 19–32 (1981).

Fois et al., Journal of Pharmaceutical Sciences, vol. 80, No. 4, pp. 363–367 (1991).

Maurer et al., Drug Metabolism And Disposition, vol. 12, No. 1, pp. 120–126 (1984).

*Primary Examiner*—Christina Y. Chan

[57] ABSTRACT

The present invention is directed to a fluorescence polarization immunoassay for cyclosporin A and metabolites thereof. The present invention also relates to novel cyclosporin A derivative compounds useful in fluorescence polarization techniques. Included among the novel compounds are cyclosporin A derivatives where the amino acid in the first position is altered. The cyclosporin A derivatives are useful in forming immunogens for raising antibodies specific to cyclosporin A and metabolites thereof.

3 Claims, No Drawings

FLUORESCENCE POLARIZATION ASSAY FOR CYCLOSPORIN A AND METABOLITES AND RELATED IMMUNOGENS AND ANTIBODIES

This application is a continuation of application Ser. No. 08/060,598, filed May 12, 1993, abandoned, which is a divisional of application Ser. No. 07/776,890, filed Oct. 15, 1991, issued as U.S. Pat. No. 5,239,057, which is a continuation of application Ser. No. 07/376,244, filed Jul. 6, 1989, abandoned, which is a continuation of application Ser. No. 07/031,494, filed on Mar. 27, 1987, abandoned.

TECHNICAL FIELD

This invention relates to a method for a fluorescence polarization immunoassay for determining the amount of cyclosporin A in fluids, especially biological fluids such as serum and whole blood, bile and the like. The invention also provides novel cyclosporin A derivatives used to raise antibodies, employed in competitive immunoassays, especially fluorescence polarization immunoassays (FPIA).

BACKGROUND OF THE INVENTION

Cyclosporin A (Cyclosporine) is a potent immunosuppressant that has been widely used in the United States and other countries to prevent the rejection of transplanted organs such as kidney, heart, bone marrow, and liver in humans. The effectiveness of cyclosporin A in the treatment of other conditions (autoimmune diseases, diabetes, malaria) is being investigated.

To prevent allograft rejections, a minimum level of cyclosporin A in the blood is required throughout the lifetime of the patient. Chronic high doses can result in kidney and liver damage. Distribution and metabolism of the drug varies greatly between individuals, as well as in a single individual during the course of therapy. Accordingly, monitoring cyclosporin A levels in the blood or serum of allograft recipients is considered essential to good patient management.

Cyclosporin A has the structure:

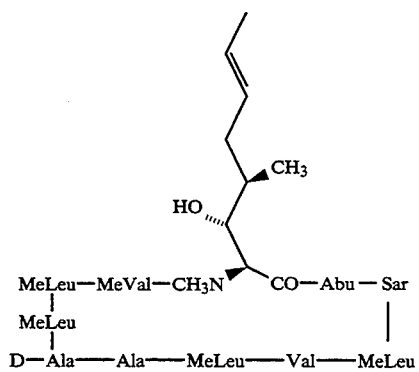

wherein the abbreviations represent:
-MeVal- a residue of N-methyl-L-valine
-MeLeu- a residue of N-methyl-L-leucine
-D-Ala- a residue of D-alanine
-Ala- a residue of L-alanine
-Val- a residue of L-valine
-Abu - a residue of L-α-aminobutyric acid
-Sar- a residue of sarcosine, also known as N-methylglycine wherein the term "residue" refers to the condensed form of the amino acid found in peptides, as is common in the art. Also, as is common in the art, the configuration of the α-amino acid is assumed to be L unless a D-configuration is specified. Cyclosporin A is a cyclic polypeptide with 11 amino acids, including an unusual 9 carbon amino acid. Cyclosporin A is described in U.S. Pat. Nos. 4,117,118 and 4,396,542.

All the metabolites of Cyclosporin A that have been identified in which the ring is still intact result from hydroxylations and dimethylations of the parent compound. [G. Maurer, H. R. Loosli, E. Schreier, B. Keller, Drug Metabolism and Disposition, 12 (1), 120–126 (1984)]. It has not yet been determined whether one or more of these metabolites is also an immunosuppressive, or the major cause of renal or hepatic toxicity. Therefore, measurement of levels of the metabolites may also be useful in patient management. Some major metabolites of cyclosporin A include metabolite 17, metabolite 18 and metabolite 21.

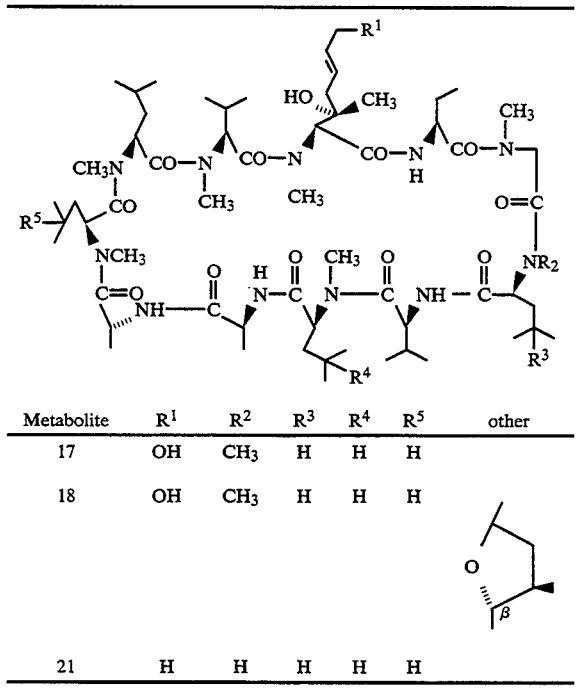

| Metabolite | $R^1$ | $R^2$ | $R^3$ | $R^4$ | $R^5$ | other |
|---|---|---|---|---|---|---|
| 17 | OH | $CH_3$ | H | H | H | |
| 18 | OH | $CH_3$ | H | H | H | (structure) |
| 21 | H | H | H | H | H | |

Presently, two analytical methods are used routinely for the monitoring of cyclosporin A: radioimmunoassay with either a $^3H$ or a $^{125}I$ tracer; or high performance liquid chromatography. G. J. Burckart, D. M. Canafox, G. C. Yee, Drug Intelligence and Clinical Pharmacy, 20, 649–652 (1986). See P. Donatsch et al., Journal of Immunoassay 2 (1), 19–34 (1981);, W. C. Mahoney, J. W. O. F., Clinical Chemistry 31, 459–462 (1985) respectively. The RIA detects cyclosporin A and some of its metabolites, and requires the handling of radioactive substances. The HPLC method is specific for cyclosporin A but is labor intensive. Both methods require excessive time. In the case of RIA a minimum of 2½ hours is required. In the case of HPLC a minimum of 30 minutes is necessary. This does not include extensive sample preparation time.

Fluorescence polarization is an alternative to radioactive methods of measuring the results of a competitive binding immunoassay. Fluorescence polarization techniques are based on the principle that a fluorescent compound, when excited by plane polarized light, will emit fluorescence having a degree of polarization inversely proportional to its rate of rotation. Small, unbound fluorescent molecules will rotate quickly and have a small degree of polarization. If the fluorescent compound is bound by a large molecule such as an antibody, the rate of rotation is slow and the degree of polarization is high. In a fluorescence polarization immunoassay, the compound(s) to be detected in the sample ("analyte"(s) or "ligand"(s)) competes with a similar compound that is attached to a fluorescent moiety ("ligand analog" or "tracer") for a limited number of receptor binding sites OD antibodies specific for the analyte(s) and tracer. If there is no analyte present, the tracer will be bound by the antibody and the degree of polarization will be large. For a given amount of analyte present, the amount of tracer bound to antibody will be correspondingly less, and the degree of polarization will be correspondingly lower. Thus, the amount of analyte present can be determined by measuring the degree of fluorescence polarization observed.

Fluorescence polarization techniques for immunoassays have been disclosed, (U.S. Pat. No. 4,420,568 to Wang et al.; U.S. Pat. No. 4,476,229 to Fino et al.; U.S. Pat. No. 4,510,251 to Kirkemo et al., each commonly assigned herewith, and others).

In the case of cyclosporin A, it is of importance to detect and quantify not only cyclosporin A but also the major metabolites thereof. The present invention is an advance in the art in that novel cyclosporin A derivative compounds specifically useful in forming immunogens to raise antibodies, and a fluorescence polarization assay using the antibodies is provided for the determination of cyclosporin A and its metabolites. The antibodies raised in response to the immunogens synthesized in accordance with the present invention are capable of specifically recognizing cyclosporin A together with some of its metabolites.

SUMMARY OF THE INVENTION

The present invention relates to novel cyclosporin A compounds substituted at and conjugated to an antigenicity-conferring carrier through a derivative formed at the first (−1) amino acid residue. Specifically, the present invention provides for cyclosporin A derivatives having an amino acid residue in the 1-position bearing a reactive functional group. The preferred carrier is a poly(amino acid), most preferably bovine serum albumin (BSA).

The present invention also relates to antibodies raised in response to the above immunogens, a method for preparing useful first amino acid residue cyclosporin A derivatives and use of the antibodies in a fluorescence polarization immunoassay to measure cyclosporine A and its metabolites.

DETAILED DESCRIPTION OF THE PREFERRED EMBODIMENT

The various aspects of the invention will now be discussed in relation to the Examples.

The present invention involves the use of fluorescein and derivatives of fluorescein. In particular, a necessary property of fluorescein and its derivatives for the usefulness of the tracer compounds is the fluorescence of fluorescein. These compounds provide the fluorescent response when excited by polarized light of an appropriate wavelength, thereby to enable the fluorescence polarization measurement to be made. Generally, the tracer compounds used in the assay provided by the present invention exist in solution as salts such as sodium, potassium, ammonium and the like, which allows the compounds to exist in the open, fluorescent form, when employed in the analytical methods of the present invention. The specific salt present depends on the buffer employed to adjust the pH level. For example, in the presence of a sodium phosphate buffer, the compounds utilized in the present invention will generally exist in the open form, as a sodium salt. Suitable fluorescein compounds for use in tracers in the invention include, for example, carboxyfluorescein, fluorescein isothiocyanates (FITC), triazinylaminofluoresceins (DTAF), 4'-aminomethylfluoroscein (AMF), and many other compounds well known in the art, including those disclosed in the art previously cited. The selection of a particular fluorescent compound for use in the tracer is a matter of choice for one skilled in the art, given the teachings hereof, and is not crucial to the practice of the present invention.

FLUORESCENCE POLARIZATION IMMUNOASSAYSS

In accordance with the method of the present invention, a sample containing cyclosporin A and metabolites, or suspected of containing cyclosporin and metabolites is intermixed with a tracer and an antibody specific for the cyclosporin A and metabolites, and the tracer. The cyclosporin A and metabolites present in the sample and the tracer compete for a limited number of antibody sites, resulting in the formation of cyclosporin A and metabolites-antibody and tracer-antibody complexes. By maintaining a constant concentration of tracer and antibody, the ratio of cyclosporin A and metabolites antibody complex to tracer-antibody complex that is formed is directly proportional to the amount of cyclosporin A and metabolites present in the sample. Therefore, upon exciting the mixture with polarized light and measuring the polarization of the fluorescence emitted by a tracer and a tracer-antibody complex, it is possible to determine quantitatively the amount of cyclosporin A and metabolites in the sample.

A tracer in solution which is not complexed to an antibody is free to rotate in less than the time required for absorption, and re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free ligand, i.e., If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture can be determined accurately. The precise relationship between polarization and concentration of the ligand to be determined is established by measuring the polarization values of calibrators with known concentrations of the ligand. The concentration of the ligand can be interpolated from a standard curve prepared in this manner.

The pH at which the method of the present invention is practiced must be sufficient to allow the tracers to exist in their ionized state. The pH may range from about 3 to 12, more usually in the range of from about 5 to 10, most preferably from about 6 to 9. Various buffers can be used to achieve and maintain the pH during the assay procedure. Representative buffers include borate, acetate, phosphate, carbonate, Tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about 0° to about 50° C., more usually from about 15° to about 40° C.

In addition to the concentration range of cyclosporin A and metabolites, considerations such as whether the assay is qualitative, semi-quantitative or quantitative, the equipment employed, and the characteristics of the tracer and antibody will normally determine the concentration of the tracer and antibody which is used. While the concentration range of cyclosporin A and metabolites in the sample will determine the range of concentration of the other reagents, i.e., tracer and antibody, normally to optimize the sensitivity of the assay, individual reagent concentrations will be determined empirically. Appropriate concentrations of the tracer and antibody are readily ascertained by one of ordinary skill in the art.

Although not forming part of the present invention, it is to be appreciated that the fluorescence polarization immunoassays for cyclosporin A and metabolites provided by the present invention can be performed especially advantageously using reagents and assay procedures, in accordance with the invention, on a TDx® Analyzer, commercially available from Abbott Laboratories, Abbott Park, Ill., from whom full details concerning operation and features of this Analyzer are available.

The present invention contemplates an antibody reagent which exhibits the needed binding characteristics for use in a fluorescence polarization immunoassay for cyclosporin A and metabolites. The antibody reagent provided by the present invention advantageously recognizes cyclosporin A together with some of its metabolites. The synthesis of the novel immunogen providing for this antibody reagent is described herein. As described below the immunogens and tracers of the present invention are formed from novel cyclosporin A derivatives having an amino acid residue in the first position bearing a reactive functional group.

By the term "reactive functional group" as used herein and throughout the accompanying claims is to be understood any group capable of reacting with an appropriate co-reacting group. In other words, a reactive functional group is a moiety which will react with other moieties to form a covalent bond. Exemplary reactive pairs include amino/ester, amino/carboxylic acid, hydroxy/carboxylic acid chloride, thio/halide or the like which provide for a covalent linkage with or without the use of a coupling agent to enable, effect or promote reaction. The term reactive functional group as used herein also envisions activated coupling groups capable for direct reaction with an appropriate co-reactive grouping, e.g. amino, hydroxy, thio group or the like so as to provide a covalent linkage without use of a coupling agent to enable, effect or promote reaction. Common leaving groups such as Cl I, Br, $N_3$, N-hydroxysuccinimidyl, 1-hydroxybenzotriazinyl can are also be components of suitable functional reactive groups as is a free hydrogen atom. Thus in the case of cyclosporin A derivatives bearing a reactive functional group this will be any group capable of reaction with a carrier molecule, e.g. protein molecule, to provide a co-valently linked conjugate with said carrier molecule, with or without requirement for use of a coupling reagent to enable, effect or promote coupling or reaction with said carrier molecule.

The Reagents

Both the immunogens and the +tracers of the present invention can be represented by the structural formula:

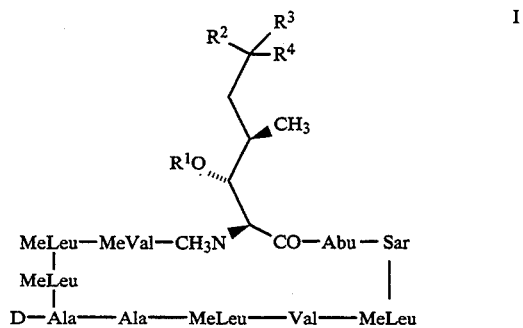

wherein (1) $R^1$ is H or a suitable hydroxyl protecting group such as $CH_3CO$, $R^2$ is H, lower alkyl or substituted lower alkyl, $R^3$ together with $R^4$ are $=W—(C=Y)_mZ$ where W is a stable chain of from 1–20 atoms (excluding H) selected from C, N, O and S, with the proviso that each heteroatom is bonded to only one other heteroatom and oxygen is never bound to another oxygen or sulfur; Y is S, O, or NH, m=0, 1 or 2; and Z is a poly(amino acid), a poly(amino acid) derivative, or a fluorescent moiety; or (2) where $R^1$ is H and $R^2$ is $W_r—(C=Y)_mZ$ where W and m are as defined above and where r=1, 0 and where Z is a poly(amino acid) or poly(amino acid) derivative or a fluorescent moiety, and $R^3+R^4$ is oxo or $R^3=R^4=H$; or (3) where $R^1=R^2=H$, $R^3$ is OH or H, and $R^4$ is $C(R^5)=W—(C=Y)_m—Z$ or $C(R^5R^6)—W_r—(C=Y)_mZ$ where W, Y, m, r & Z are defined as above, and $R^5$ and $R^6$ are H, lower alkyl, or substituted lower alkyl. Where Z is a poly(amino acid) or poly(amino acid) derivative, the compound is an immunogen; where Z is a fluorescent moiety the compound is a tracer. In the case of (1)–(3) above the compound is a precursor for a tracer or immunogen where Z is OH, $NH_2$, $NHNH_2$, or $OR_a$, $SR_a$, $NHR_a$, $NR_aR_b$ (where $R_a$ and $R_b$ are stable chains of from 1–10 carbon atoms), SH or a leaving group such as Cl, I Br,$N_3$, N-hydroxysuccinimidyl, 1-hydroxybenzotriazinyl or H when m≠0.

More specifically the tracers and immunogens in accordance with the present invention are represented by the structural formula

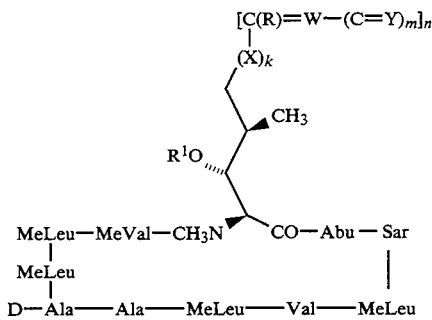

where n is 0 or 1;
k is 0 or 1, with the provision that only when n is 1 may k be 0, X is $CH_2$, CHOH, or C=O when n is 0;
m is 0, 1 or 2;
p is 1;
R is H, lower alkyl or $CH(OH)CH_3$;
$R^1$ is H or a suitable hydroxyl protecting group such as $CH_3CO$;
W is 1–20 atoms (not including hydrogen) selected from C, N, O and S, with no more than two heteroatoms bonded together and with oxygen never bound to another oxygen or sulfur;
Y is O, S, or NH; and
Z is a poly(amino acid) or poly(amino acid) derivative or a fluorescent moiety. Where Z is a poly(amino acid) or poly(amino acid) derivative, the compound is an immunogen; where Z is a fluorescent moiety the compound is a tracer. Further, where Z is OH, $NH_2$, $NHNH_2$, $OR_a$, $SR_a$, $NHR_a$, $NR_aR_b$ (where $R_a$ and $R_b$ are stable chains of from 1–10 carbon atoms), SH or a leaving group such as Cl, I, Br, $N_3$, N-hydroxysuccinimidyl, 1-hydroxybenzotriazinyl or H when m≠0, the above structure represents a precursor for tracers and/or immunogens. Also, in the case of precursor compounds X may equal $CH_2OH$ when p is 0.

Most preferably, the tracers and immunogens are represented by the structural formula:

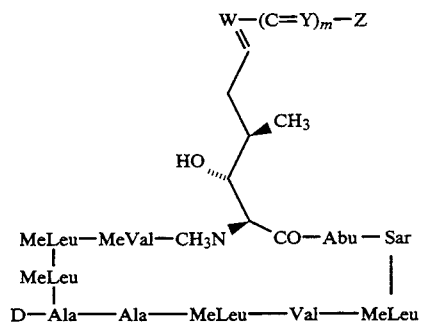

where W is 1–20 atoms, not including hydrogen, selected from C, N, O and S, with no more than two heteroatoms bonded together and with oxygen never bound to another oxygen or sulfur;

Y is O, S, or NH;
m is 0, 1 or 2; and
Z is a poly(amino acid) or poly(amino acid) derivative or a fluorescent moiety. Where Z is a poly(amino acid) or poly(amino acid) derivative, the compound is an immunogen; where Z is a fluorescent moiety the compound is a tracer. Further, where Z is OH, $NH_2$, $NHNH_2$, $OR_a$, $SR_a$, $NHR_a$, $NR_aR_b$ (where $R_a$ and $R_b$ are stable chains of from 1–10 carbon atoms), SH or a leaving group such as Cl, I, Br, $N_3$, N-hydroxysuccinimidyl, 1-hydroxybenzotriazinyl or H when m≠0, the above structure represents a precursor for tracers and/or immunogens.

The structures of the immunogens and tracers are such that there is a competition between cyclosporin A and the tracer for the binding sites of the antibody. Various structures of immunogens and tracers are allowed. For the purposes of this invention, "haptens" are precursors of the immunogens, comprised generally of cyclosporin A, which is derivitized at the first amino acid residue (i.e., 9-carbon amino acid).

1. The Antibodies

The antibodies of the present invention are prepared by developing an immune response in animals to the immunogens described below. The immunogen is administered to animals such as rabbits or sheep by a series of injections, in a manner known to those skilled in the art.

a. Structure of the Immunogens

The general form of the immunogen has the formula II where n is 0 or 1;
k is 0 or 1, with the provision that only when n is 1 may k be 0;
X=$CH_2$, CHOH or C=O when n is 0;
m is 0, 1, or 2;
p is 0 or 1;
R is H or lower alkyl, or $CH(OH)CH_3$
$R^1$ is H or a suitable protecting group such as $CH_3CO$;
W is 1–20 atoms (not including hydrogen) selected from C, N, O and S, with no more than two heteroatoms bonded together and with oxygen and sulfur never bound to another oxygen or sulfur;
Y=O, S, or NH; and
Z is poly(amino acid).

The preferred form of the immunogen is shown in formula III where W is 1–20 atoms, not including hydrogen, selected from C, N, O and S, with no more than two heteroatoms bonded together and with oxygen never bound to another oxygen or sulfur;
Y is O, S, or NH
m is 0, 1 or 2
Z is poly(amino acid)

This structure is preferred because best recognition of both cyclosporin A and its metabolites #17 and #18 will occur if the portions of the structures which are common to both cyclosporin A and its metabolites are exposed to antibody recognition, while the portions of the structures which distinguish cyclosporin A from its metabolites are hidden from antibody recognition. This masking of structural differences is achieved by attaching the portion of the structure to be hidden directly to the poly(amino acid). Bovine serum albumin is the poly(amino acid) in this preferred form, but it should be understood that other protein carriers can be employed, including albumins and serum proteins, e.g., globulins, lipoproteins, and the like. Illustrative protein carriers include bovine serum albumin, keyhole limpet hemocyanin, egg ovalbumin, bovine gamma globulin, thyroxine binding globulin, etc. Alternatively, synthetic poly(amino acids) can be prepared having a sufficient number of amino groups incorporated, such as in polylysine.

The immunogens can be prepared by coupling a compound of the class shown in II above modified with Z=H, Cl, OH, NHNH$_2$ or NH$_2$ to a poly(amino acid) or a derivative of a poly(amino acid) as will be discussed in the context of the synthetic method and the Examples below.

b. Synthesis of the Immunogens

The immunogens of the present invention can be made from a precursor having a structure shown in Formula II where Z is H or a reactive functional group such as NH$_2$, NHNH$_2$, OH, Cl, Br or I. The immunogens of the present invention are made by coupling a hapten, such as that shown in Formula II, to a poly(amino acid). The poly(amino acid) can be linked to the hapten by an activated coupling group such as an amide, an amidine, an alkyl, a urea, a thiourea, a carbamate, or a thiocarbamate linkage. In the preferred embodiment, the poly(amino acid) is bovine serum albumin (BSA), and the immunogen precursor has the structure:

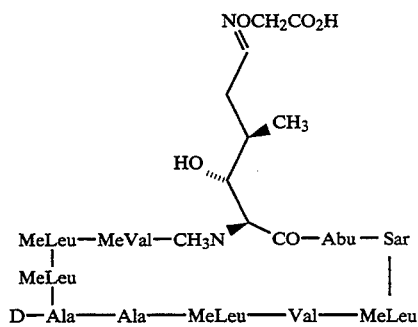

IV

The hapten is coupled to the BSA, preferably under conditions normally used to form amide bonds; such conditions are well-known to those skilled in the art, and may use as the coupling agent a carbodiimide, especially a water soluble carbodiimide such as 1-ethyl-3(3-dimethylaminopropyl)carbodiimide (EDC) or 1-cyclohexyl-3-(2-morpholinoethyl)carbodiimide metho-p-toluenesulfonate. The same reagents can be used in the case where there is a —C—NH$_2$, or —NHNH$_2$ group on the hapten, in which case an amide bond is formed with a-CO$_2$H group on the BSA. When Z=CNOR, NCO, NCS, OCOCl, Br or I, the poly(amino acid) is mixed directly with the hapten.

The haptens can be prepared from a single aldehyde precursor, having the formula:

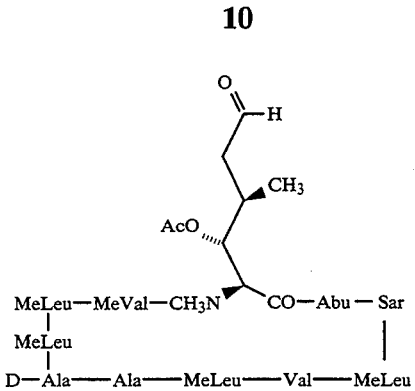

V

This aldehyde is prepared by first protecting the hydroxyl group of cyclosporin A with a suitable protecting group such as acetyl. The olefin can then be oxidatively cleaved to form the aldehyde, which is a versatile intermediate. This aldehyde can be reacted with a Wittig Reagent ($\phi_3$P=CHR) or modification thereof such as (carbethoxymethylene)triphenylphosphorane. Preferably, triethylphosphonoacetate is used. The aldehyde can be oxidized to the corresponding carboxylic acid or reductively aminated to the corresponding amine. Both of these compounds can be used as haptens. Other transformations of the aldehyde into useful haptens are obvious to one who is skilled in the art. In the preferred embodiment of the present invention, the aldehyde is reacted with an O-substituted hydroxylamine, such as O-(carboxymethoxyl)amine hemihydrochloride in the presence of a base such as sodium bicarbonate, to form the oxime. Deprotection of the hydroxyl group under mildly basic conditions gives the hydroxy carboxylic acid shown in Formula IV, which is suitable for immunogen preparation.

2. The Tracers a. The Structure of the Tracers

The tracers useful in the present invention have the general structural formula shown in Formula I, as defined previously, except that Z=Fl, where Fl represents a fluorescent moiety. The preferred form of the tracers is shown in Formula II, as defined in the previous section, except that Z=Fl. Most preferably the tracers have the structure shown in Formula III, as defined in the previous section, except that Z=Fl.

The tracer is a cyclosporin A derivative that is linked to a fluorescent moiety through a coupling group, for example, an amido, amidino, triazinylamino, carbamido, thiocarbamido, carbamoyl, thiocarbamoyl, or sulfonylcarbamoyl group. The tracers are prepared by linking the appropriate fluorescent compound to a cyclosporin A derivative containing an amino, carboxylic acid, hydroxy, imidate, hydrazide, isocyanate, thioisocyanate, chloroformate, chlorothioformate, chlorosulfonylcarbamoyl, or the like group, as will be discussed in the context of the synthetic method and the Examples below.

By way of Example, any of the following fluorescein derivatives can be used:

| | |
|---|---|
| Fl—NH— | fluoresceinamine |
| Fl—CH$_2$NH$_2$— | aminomethylfluorescein |
| FlCO$_2$H | carboxyfluorescein |
| Fl—NHCOCH$_2$I | α-iodoacetamidofluorescein |

-continued

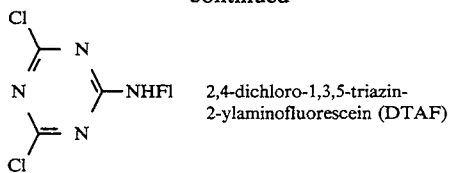

2,4-dichloro-1,3,5-triazin-2-ylaminofluorescein (DTAF)

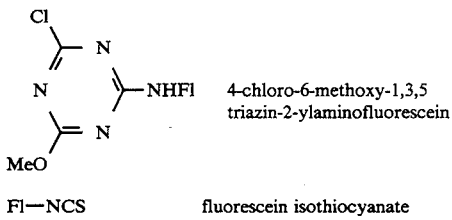

4-chloro-6-methoxy-1,3,5 triazin-2-ylaminofluorescein

Fl—NCS    fluorescein isothiocyanate b. Synthesis of the Tracers

The tracers of the present invention are prepared by coupling a fluorescent compound, preferably a derivative of fluorescein, to the general structure shown in Formula II, where Z is H, OH, Br, Cl I, $NH_2$, or $NHNH_2$ and p is 1.

The fluorescent moiety can be linked to the amino, carboxyl, imidate or alkoxy functional group by an amide, an amidine, a urea, a thiourea or sulfonylcarbamate linkage. In the presently preferred embodiment, the fluorescein derivative is aminomethyl fluorescein, and this is coupled to the tracer precursor shown below:

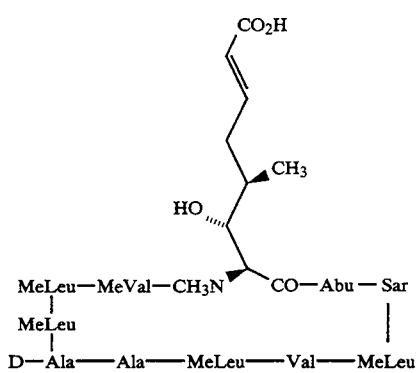

VI using standard peptide coupling techniques in a suitable solvent such as N,N-dimethyl-formamide (DMF). Standard peptide coupling techniques are known to those skilled in the art, and often utilize an N,N'-disubstituted carbodiimide and an additive such as N-hydroxysuccinimide, 1-hydroxybenzotriazole, or p-nitrophenol. These additives form a stable but activated ester capable of reacting with an amino moiety. The structure depicted in Formula VII below shows the preferred tracer useful in the present invention.

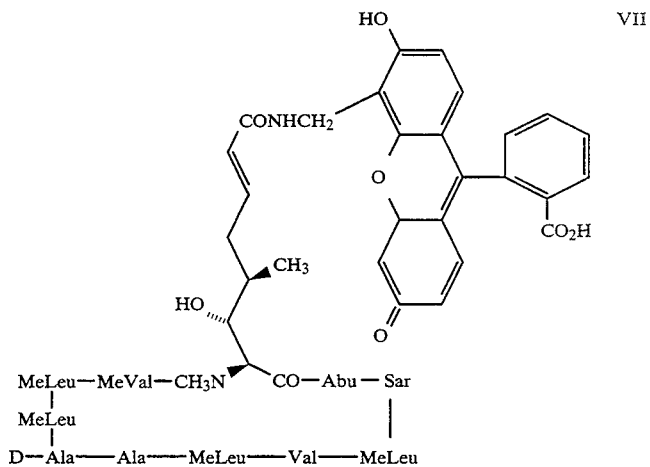

VII

The tracer precursor depicted in Formula VI is also obtained from the aldehyde depicted in Formula V, by a treatment with $(EtO)_2POCH_2CO_2Et$ in the presence of a base, followed by removal of the acetyl and hydrolysis of the ester under standard basic conditions.

3. The Pretreatment Solution

The method of measuring the concentration of cyclosporin A and metabolites by fluorescence polarization immunoassay techniques is described herein at Example 3 and employs a novel pretreatment solution. Specifically the pretreatment solution includes a precipitation reagent of from about 15 to about 45 mM ammonium acetate in from about 97.7 to about 99.2% aqueous isopropanol.

EXAMPLE 1

Preparation of Cyclosporin A Immunogen

For purposes of this example, compounds named are followed by an arabic numeral which designates that compound when later referenced in the Example.

(a) Immunogen Precursor Compounds

[3-(R)-acetoxy-4-(R)-methyl-2-(S)-methylamino-6-oxo-hexanoyl][1] cyclosporin A 1

[3-(R)-acetoxy-7-hydroxy-4-(R)methyl-2-(S)-methylamino-6-oxo-octanoyl][1] cyclosporin A 2

[3-(R)-acetoxy-6-hydroxy-4-(R)methyl-2-(S)-methylamino-7-oxo-octanoyl][1] cyclosporin A 3

Acetyl Cyclosporin A (obtained from cyclosporin A according to the procedure by R. Traber, et al. Helv. Chim. Acta, 65, Fasc 0.5 (1982)#16., p. 1655-1677)) (984 mg) was dissolved in a mixture or 5.5 ml of dioxane and 2.0 ml of $H_2O$. Three drops of a solution of 1.0 g of osmium tetraoxide in 10 ml of $H_2O$ was added and the mixture was stirred at room temperature for 5 minutes. During this time the reaction turned a dark grey color. Sodium periodate (388 mg) was added and the reaction was stirred at room temperature from 2 hours to 24 hours. The reaction solution was concentrated and the residue was taken up into 15 ml of H₂O, which was extracted with 2×40 ml of EtOAc. The combined EtOAc extracts were washed with 1×5 ml of saturated NaCl solution, dried over anhydrous Na₂SO₄, filtered and concentrated. The residue was chromatographed on silica gel using 3% MeOH/CH₂Cl₂ to elute the column. The aldehyde was found to be purest in the initial fractions. Later fractions were a mixture of the aldehyde and the hydroxy ketones. The combined yield was 78%, with the ratio of aldehyde 1 to hydroxy ketones ⅔ being approximately 3:2.

[3-(R)-acetoxy-4-(R)-methyl-2-(S)-methylamino-6-(carboxymethyloximino-hexanoyl]¹ cyclosporin A 4

[3-(R)-acetoxy-4-(R)-methyl-2-(S)-methylamino-6-oxo-hexanoyl]¹ cyclosporin A 1 (700 mg) was dissolved in 8.7 ml of absolute ethanol, along with sodium bicarbonate (500 mg) and carboxymethoxylamine hemihydrochloride (252 mg), and stirred at room temperature overnight. The reaction was then concentrated and 2 ml of H₂O and 5 ml of ethyl acetate were added to the residue. After the pH of the aqueous layer had been adjusted to pH 2 with 1M H₃PO₄, the layers were separated and the aqueous layer was further extracted with 2×5 ml of ethyl acetate. The combined organic extracts were washed with saturated NaCl solution, dried over anhydrous MgSO₄, filtered and concentrated. The residue was chromatographed on silica gel using 95 CH₂Cl₂: 4 methanol: 1 acetic acid. The product was obtained in 85% yield as a mixture of syn and anti isomers, The isomers could be separated by chromatography on silica gel, eluting with 95 Et₂O: 4 MeOH: 1AcOH. Each isomer was obtained in 37% yield.

[6-(carboxymethyloximino)-3-(R)-hydroxy-4-(R)-methyl-2-(S)-methyl-aminohexanoyl]¹ cyclosporin A 5

[3-(R)-acetoxy-6-(carboxymethyloximino)-4-(R)-methyl-2-(S)-methylaminohexanoyl]¹ cyclosporin A 4 (140 mg) was dissolved in methanol (4.0 ml) along with potassium carbonate (90 mg). The reaction was stirred at room temperature overnight. The solvent was removed under reduced pressure at 30° C. and H₂O was added The pH was adjusted to 3.0 with 1M H₃PO₄ and the solution was extracted with 3×15 ml of ethyl acetate. The combined organic extracts were washed with 1×5 ml of saturated NaCl solution, dried over anhydrous MgSO₄, and concentrated. The product was chromatographed on silica gel using 95 CH₂Cl₂: 4 MeOH: 1AcOH as eluent to remove a small amount of a less polar impurity. Yield was 89 mg. (64%).

[3-(R)-acetoxy-6-(carboxymethyloximino)-7-hydroxy-4-(R)-methyl-2-(S)-methylaminoctanoyl]¹ cyclosporin A 6 and
[3-(R)-acetoxy-7-(carboxymethyloximino)-6-hydroxy-4(R)-methyl-2-(S)-methylaminooctanoyl]¹ cyclosporin A 7

The procedure described above for compound 4 is followed using a mixture of the aldehyde 1 and the hydroxy ketones 2 and 3. Chromatography on silica gel using 95.5 CH₂Cl₂: 3.5 MeOH: 1AcOH separated the aldoxime (Rf 0.14) from the ketoximes (Rf 0.095)

[6-carboxymethyloximino)-3-(R), 7-dihydroxy-4(R)-methyl-2(S)-methylaminooctanoyl]¹ cyclosporin A 8 and [7-carboxymethyl-oximo)-3-(R), 6-dihydroxy-4(R)-methyl-2(S)methylaminooctanoyl]¹ cyclosporin A 9

The procedure for compound 5 was followed using the ketoxime 6 and 7 as starting materials. Upon evaporation of the organic extracts, a white foam was obtained in 92% yield, Rf 0.11 (silica gel, 95 CH₂Cl₂: 4MeOH: 1AcOH, 2 elutions).

[3-(R-acetoxy-7-ethoxycarbonyl-4-(R)-methyl-2-methyl-amino-6-heptenoyl]¹ cyclosporin A 10

The aldehyde 1 (1.12 g) was dissolved in 4.0 ml of tetrahydrofuran and 1 ml of H₂O. Potassium carbonate (500 mg) and triethylphosphonoacetate (1.0 ml) were added, and the run was stirred at 35°–40° C. for 7 days. The reaction could be monitored by 60 MHz NMR of concentrated reaction aliquots in the 9–10 region, where the presence of the aldehydic proton could be observed. The reaction was neutralized with 1M H₃PO₄ and poured into 75 ml of ethyl acetate. The layers were separated and the organic layer was washed with 3×10 ml of H₂O and 2×10 ml of saturated NaCl solution. The organic layer was dried over anhydrous MgSO₄, filtered and concentrated. The yellow liquid residue was purified by flash chromatography on silica gel using 96.5 CH₂Cl₂: 3.5 MeOH (v/v) as eluent. The product was obtained with a slight contamination of the starting aldehyde, 1.0 g, 84% yield.

[7-Methoxycarbonyl-3-(R)-hydroxyl-4(R)-methyl-2-(S)-methylamino-6-heptenoyl]¹ cyclosporin A 11

The ester 10 (300mg) was dissolved in 5 ml of methanol, and potassium carbonate (190 mg) was added. The slightly yellow solution was stirred at ambient temperature for 3 days. The apparent pH of the reaction was adjusted to 4–5 with 1M H₃PO₄ and the solution was partitioned between 20 ml of EtOAc and 5 ml of H₂O. The layers were separated and the aqueous layer was further extracted with 2×10 ml of EtOAc. The combined organic extracts were washed with 1×5 ml of saturated NaCl solution, dried over anhydrous MgSO₄, filtered and concentrated. The residue was purified by silica gel chromatography on a Chromatotron (Harrison Research; 810 Moana Court, Palo Alto, Calif.), using a 1 mm rotor and eluting with 97 CH₂Cl₂: 3MeOH (v/v). The least polar component (Rf 0.21) was the desired product. Yield 93 mg, 32%.

[7-carboxyl-3-(R)-hydroxy-4-(R)-methyl-2-(S)-methylamino-6-heptenoyl]¹ cyclosporin A 12

The hydroxy ester 11 (105 mg) was dissolved in 3 ml of methanol, 0.5 ml of H₂O and 0.5 ml of 1N NaOH. The reaction was stirred at ambient temperature for 3 hours. The pH was then adjusted to pH 2 with 1M H₃PO₄ and the solution was extracted with 4×20 ml of ethyl acetate. The combined organic layers were washed with 3×10 ml of H₂O and 1×10 ml of saturated NaCl solution, dried over anhydrous MgSO₄, filtered and concentrated to give 80 mg of residue. The crude product was purified by preparative thin layer silica gel chromatography using 95 CH₂Cl₂: 4 MeOH: 1AcOH as the solvent system. The band at Rf 0.3 was collected and the absorbent was washed with methanol. Concentration of the methanol gave 71 mg of the carboxylic acid 12, 67% yield.

(b) Preparation of Immunogen

The carboxylic acid 5 (50 mg) was dissolved in dimethylsulfoxide (2.5 ml). Bovine serum albumin (25 mg) was dissolved in 0.1M NaHCO$_3$ buffer at pH 8.0 (2.5 ml). The DMSO solution was slowly dissolved into the aqueous solution with stirring. The pH was then adjusted to 8.0 with 1N HCl. 1-Ethyl-3(-3-dimethylaminopropyl)carbodiimide hydrochloride (300 mg), dissolved in water (0.5 ml), was added to the BSA-hapten solution over 20 minutes in 50 ul aliquots. The reaction was stirred at ambient temperature for 16 hours. The reaction mixture was then dialyzed against 50% DMSO/H$_2$O (250 ml), 25% DMSO/H$_2$O (250 ml) and 100% H$_2$O (2×250 ml). The resulting dialyzed material containing immunogen was used to immunize experimental animals.

EXAMPLE 2

Preparation of Cyclosporin A Tracer

[7-(Fluoresceinylmethylaminocarbonyl)3-(R)-hydroxy-4(R)methyl-2-(S)-methylamino-6-heptenoyl][1] cyclosporin A 13

The acid 12 in Example 1 (7.3 mg) was dissolved in dimethylformamide (100 ul). N-Hydroxybenzotriazole hydrate (2.5 mg) and N,N'-diisopropylcarbodiimide (2.0 ul) were added, and the reaction was stirred at ambient temperature overnight. Aminomethylfluorescein hydrochloride (2.3 mg) and diisopropylethylamine (1 drop) were added to the solution containing the active ester. The reaction was stirred for 24 hours at ambient temperature. The solvent was removed in vacuo and the residue was purified by thin-layer silica gel, chromatography (3×95 CH$_2$Cl$_2$: 5 MeOH, Rf 0.92, then 95 EtOAc: 5 MeOH, Rf 0.37).

EXAMPLE 3

Cyclosporin A Assay

A. Reagents

The reagents for the fluorescence polarization assay of the present invention comprise antibody specific for cyclosporin A and metabolites raised in response to the immunogen made from the hapten in Formula IV and the aminofluorescein tracer in Formula VII. Additionally, a cyclosporin A and metabolites pretreatment solution (isopropanol and NH$_4$ acetate), a dilution buffer, cyclosporin A and metabolites calibrators and cyclosporin A and metabolite controls are desirably prepared.

The tracer formulation presently preferred is 48 nanomolar tracer in 0.1 molar tris buffer at pH 7.5; 0.1% (weight/volume) sodium dodecyl sulfate, 0.1% sodium azide, and 0.01% bovine gamma globulin. The antiserum formulation comprises rabbit serum diluted with phosphate buffered saline containing 2% ethylene glycol (volume/volume) 0.1% sodium azide (weight/volume) and 1% normal sheep serum. The dilution buffer comprises 0.1 molar sodium phosphate at pH 7.5; 0.1% (weight/volume) sodium azide; and 0.01% (weight/volume) bovine gamma globulin. The pretreatment formulation comprises 0.1 molar tris buffer at pH 7.5; 0.1% (weight/volume) sodium azide; 0.5% (weight/volume) copper sulfate; and 10.0% (weight/volume) 5-sulfosalicylate. The precipitation reagent comprises 30 mM ammonium acetate in 98.5% aqueous isopropanol. Cyclosporin A and metabolites calibrators comprising cyclosporin A and normal human serum are provided at concentrations of 0.0, 50, 100, 200, 500 and 1000 nanograms per milliliter, with 0.1% sodium azide preservative. Cyclosporin A and metabolites controls comprising cyclosporin A and normal human serum are provided at concentrations of 75, 250 and 700 nanograms per milliliter, with 0.1% sodium azide preservative.

B. Assay Protocol

Because of the very high binding of cyclosporin A and metabolites to proteins (especially lipoproteins), an extraction step is employed which precipitates the proteins in a sample while recovering 100±10% of the cyclosporin A and metabolites present. However, the assay is a homogeneous assay, which means that the fluorescence polarization readings are taken from a solution in which bound tracer is not separated from unbound tracer. This is a distinct advantage over radioimmunoassay procedures, for example, where the bound radioactive tracer must be separated from the unbound radioactive tracer before a reading can be taken.

According to the preferred assay procedure of the present invention, cyclosporin A and metabolites calibrators, controls and unknown samples must be prepared by the same procedure. In the preferred procedure, which is designed to be used in conjunction with the Abbott TDx ® Analyzer, 50 microliters of the serum or plasma sample are pipetted into a labeled centrifuge tube. A pipette, such as a TDx ® Precision Dispenser, is filled with precipitation reagent and purged of air bubbles. One hundred and fifty microliters of precipitation reagent are then dispensed into each centrifuge tube by touching the end of the dispensing syringe tip to the wall of the centrifuge tube while releasing the solution. After all samples are pipetted, each centrifuge tube is capped and then mixed on a vortex mixer for ten seconds. The tubes are then placed into a centrifuge head. The tubes should be evenly distributed so that the centrifuge head is balanced. The samples are then centrifuged for at least three minutes at 9,500×g, or until clear supernatant and a hard, compact pellet of denatured protein is obtained. After centrifugation is complete, each tube is uncapped and the supernatant is decanted into the corresponding sample well of a TDx ® Sample Cartridge or equivalent. Since 150 microliters of sample supernatant are required to perform the assay in accordance with the preferred TDx assay procedure, care must be taken when decanting to transfer the last drop of supernatant into the sample well. This can be accomplished by tapping the centrifuge tube on the edge of the sample cartridge. If the TDx ® Cyclosporine and Metabolites Assay Kit is being used with the TDx Analyzer, the caps from each of the three vials in the TDx ® Cyclosporine and Metabolites Reagent pack are removed and placed into designated wells inside the reagent pack, the reagent pack is placed inside the TDx ® Analyzer, and the assay procedure from this point is fully automated.

If a manual assay is being performed, then the treated sample is mixed with dilution buffer. The antibody and the pretreatment solution are placed into the test tube containing the sample, and a background fluorescence reading is taken. Then tracer and dilution buffer are added to the sample, and after incubation, a fluorescence polarization reading is taken.

The fluorescence polarization value of each calibrator, control or sample is determined and is printed on the output tape of an instrument such as the Abbott TDx ® Analyzer. A standard curve is generated in the instrument by plotting the polarization, P, of each calibrator versus its concentration using a nonlinear regression analysis. The concentration of each control and sample is read off the stored calibration curve and printed on the output tape.

The sensitivity of the preferred fluorescence polarization assay is 15.0 nanograms/milliliter of cyclosporin A and metabolites. When compared to an available radioimmunoassay using 208 clinical samples, a linear least squared regression analysis gave a slope of 1.153, an intercept of 21.06, and a correlation coefficient of 0.813.

It should be understood that the foregoing detailed description and Examples are intended to be illustrative, but not limiting, with respect to the scope of the present invention. Various modifications will become apparent to one skilled in the art, and thus it is intended that the scope of the invention be defined by the claims and equivalents thereto.

We claim:

1. A method for determining cyclosporin A and metabolites in a sample, said method comprising:
    (a) intermixing said sample with a fluorescent labeled tracer wherein said fluorescent labeled tracer is

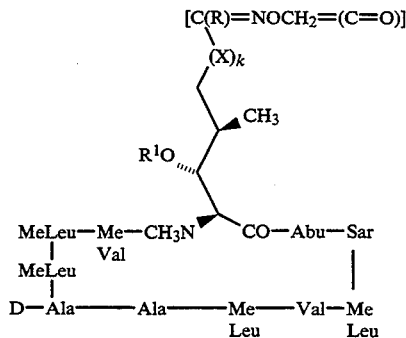

wherein
k is 0 or 1,
X is $CH_2$, CHOH or $CH_2OH$,
R is H, lower alkyl or $CH(OH)CH_3$,
$R^1$ is H or a suitable protecting group, and
Z is a fluorescent moiety, or

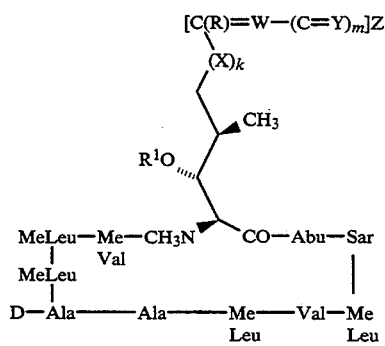

wherein
k is 0 or 1,
X is $CH_2$ or CHOH,
m is 1 or 2,
R is H, lower alkyl or $CH(OH)CH_3$,
$R^1$ is H or a suitable protecting group,
W is 1–20 atoms selected from C, N, O and S, with no more than two heteroatoms bonded together and with oxygen never bound to another oxygen or sulfur,
Y is O, S or NH, and
Z is a fluorescent moiety;
and an antibody capable of specifically binding cyclosporin A and metabolites thereof and said tracer; and
    (b) determining the amount of tracer bound to antibody by fluorescence polarization techniques as a measure of the amount of cyclosporin A and metabolites in the sample.

2. A process for measuring the concentration of cyclosporin A and metabolites thereof comprising the steps of:
    (a) contacting a sample with cyclosporin A and metabolite antiserum and with a fluorescent tracer compound wherein said fluorescent tracer compound is

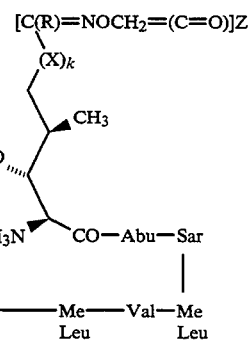

wherein
k is 0 or 1,
X is $CH_2$, CHOH or $CH_2OH$,
R is H, lower alkyl or $CH(OH)CH_3$,
$R^1$ is H or a suitable protecting group, and
Z is a fluorescent moiety, or

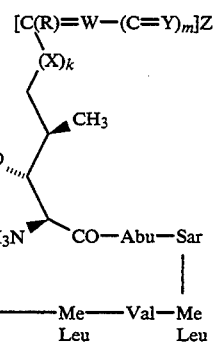

wherein
k is 0 or 1,
X is $CH_2$ or CHOH,
m is 1 or 2,
R is H, lower alkyl or $CH(OH)CH_3$,
$R^1$ is H or a suitable protecting group,
W is 1–20 atoms selected from C, N, O and S, with no more than two heteroatoms bonded together and with oxygen never bound to another oxygen or sulfur,
Y is O, S or NH, and
Z is a fluorescent moiety;

(b) passing plane polarized light through the resulting solution from step (a) to obtain the fluorescence polarization response; and (c) detecting the fluorescence polarization response of the solution of step (b) as a measure of the amount of cyclosporin A and metabolites in the sample.

3. The process of claim 2, wherein the cyclosporin A antiserum is produced by antibodies raised in response to an immunogen made from a hapten having the formula:

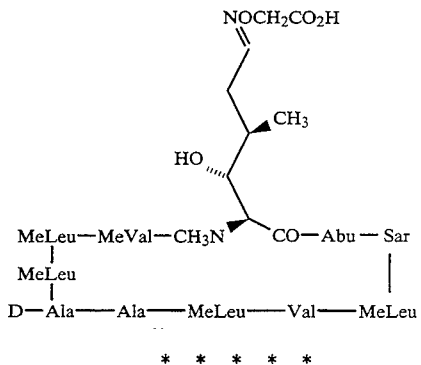

* * * * *